(12) United States Patent
Cush

(10) Patent No.: US 8,198,216 B2
(45) Date of Patent: Jun. 12, 2012

(54) GRANULAR FORMULATION

(75) Inventor: Randall C. Cush, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 625 days.

(21) Appl. No.: 12/293,097

(22) PCT Filed: Mar. 26, 2007

(86) PCT No.: PCT/US2007/064907
§ 371 (c)(1),
(2), (4) Date: Nov. 25, 2008

(87) PCT Pub. No.: WO2007/112339
PCT Pub. Date: Oct. 4, 2007

(65) Prior Publication Data
US 2009/0305889 A1    Dec. 10, 2009

Related U.S. Application Data

(60) Provisional application No. 60/786,265, filed on Mar. 27, 2006.

(51) Int. Cl.
*A01N 59/04* (2006.01)
*A01N 3/02* (2006.01)
*A01N 25/00* (2006.01)
*A01N 65/00* (2009.01)
*A01N 33/00* (2006.01)

(52) U.S. Cl. ............... 504/101; 504/113; 504/116.1; 504/189; 504/326

(58) Field of Classification Search ............... 504/101, 504/113, 116.1, 189, 326
See application file for complete search history.

(56) References Cited

U.S. PATENT DOCUMENTS 5,300,529 A * 4/1994 Narayanan .................. 514/788
6,375,969 B1 * 4/2002 Kostka et al. ............... 424/409
2005/0043182 A1 * 2/2005 Douglass et al. ............. 504/363

OTHER PUBLICATIONS

Database CAPLUS on STAN AN:2000:718303, "Synergistic imidacloprid insecticide and its preparation,"Liu et al., see Abstract.
Database CAPLUS on STN. AN:1937:26067, "Plant-protecting compostions," Kaysing, see Abstract.

* cited by examiner

*Primary Examiner* — Johann Richter
*Assistant Examiner* — Jane C Oswecki
(74) *Attorney, Agent, or Firm* — William A. Teoli, Jr.

(57) ABSTRACT

A dry spreadable or broadcast granule having an applied composition comprising an active chemical agent capable of forming a microemulsion upon dilution with water.

31 Claims, No Drawings

GRANULAR FORMULATION

This application is a 371 of International Application No. PCT/US2007/064907 filed Mar. 26, 2007, which claims priority to U.S. 60/786,265 filed Mar. 27, 2006, the contents of which are incorporated herein by reference.

This invention relates to dry spreadable or broadcast granule compositions; their use as carriers of active chemical agents, such as herbicides, insecticides and other pesticides; and methods for preparing and using said compositions. More specifically, the technology relates to a formulation for use in the form of dry granules and methods of preparing the same, and even more specifically for their use in the spreadable or broadcast delivery of active chemical agents to soil and/or vegetation.

BACKGROUND OF THE INVENTION

A pesticide is a bioactive material which destroys or inhibits the action of plant or animal pests. The general term pesticide includes insecticides, herbicides, fungicides, plant growth regulators, rodenticides and miticides.

Pesticides are widely used in soil and foliar applied to desired plants, such as ornamentals, plants grown for food and fiber and turf, for the control of weeds, insects and disease. Typically, pesticides are formulated into conventional forms such as dusts, granules, wettable powders and emulsions using techniques well known in the art. A preferred means of applying pesticides for both consumers and professional applicators is dry granules for use in the broadcast delivery of the pesticides.

Granular pesticides are important commercial products because of their ability to eliminate undesirable vegetation, diseases, insects and the like and their ease of application, either by hand or a mechanical means. The granular pesticide can be a pesticide applied to an inert material, like clay or ground corn cobs, or can be a combination fertilizer/pesticide, wherein the pesticide is applied to a fertilizer material.

In a granular form, a pesticide is impregnated into or absorbed onto an inert material or a fertilizer material. The granular pesticide product is applied to soil and/or vegetation by directly spreading pesticide granules onto the soil and/or vegetation at a suitable dosage rate.

The dry granules of the present invention are those granules which can be applied with a dry spreader or by hand to a target area and when exposed to water by way of, for example, rain or irrigation, will allow the pesticide material to migrate further away from the carrier. The granules of the present invention include inert carriers that do not disintegrate readily upon watering. In order to facilitate the spreading of the pesticide, granules of the present invention may also be prepared so as to readily disintegrate when exposed to water and spread thus increasing the area affected by the pesticide. These granules are often prepared from wood dust, diatomaceous earth compositions or mineral components, such as limestone or dolomite, and may contain surfactants and/or binders to aid in the disintegration and dispersion of the granules upon exposure to water. Granules for delivering pesticides also include fertilizers impregnated with a pesticide.

Microemulsions, another conventional formulation for active chemical agents, are a subclass of emulsions and are a thermodynamically stable dispersion of one liquid phase into another, stabilized by an interfacial film or surfactant. Microemulsions are typically clear solutions and contain emulsion droplets having an average particle size of about 0.01 to 0.1 microns. These formulations typically contain an oil phase comprising at least one pesticidally active ingredient and emulsifiers. Substantially water-insoluble pesticides that are liquid at room temperatures can be dispersed as they are in water. When the active ingredients are solid or of high viscosity, water immiscible organic solvents may be used to dissolve them. Typically, the amount of emulsifiers needed in a microemulsion is higher than that in an emulsion. Microemulsifiable concentrates contain high levels of active ingredients and emulsifier and upon dilution in water form compositions containing emulsion droplets having an average particle size of about 0.01 to 0.1 microns. One or more emulsifiers may be used in preparing the microemulsifiable concentrates of the present invention. The concentrates can comprise a single surfactant, for example, a non-ionic surfactant such as a condensation product of castor oil and a poly-$C_{2-4}$alkylene oxide. Combinations of strongly hydrophobic non-ionic surfactants (preferably those having a hydrophilic-lipophilic balance (HLB)>13) and hydrophobic anionic surfactants are also preferred emulsifiers for microemulsions and microemulsifiable concentrates.

Microemulsions and microemulsifiable concentrates are well known in the art as shown by, for example, European Patent Application No. EP 160 182 A2; U.S. Pat. Nos. 4,870,103; 4,904,695; 4,954,338; 4,973,352; 5,242,907; 5,317,042; 5,326,789; 5,334,585; U.S. Patent Application Publication Nos. 2003/087764, 2004/0132621 and 2005/0043182; PCT Publications WO 99/65300 and WO 02/45507.

The granular pesticides of the present invention comprise a pesticide or mixture of pesticides blended in, absorbed, impregnated or coated onto a solid substrate. The solid substrate can be an inert material, for example, clay, and/or a fertilizer material, for example, urea/formaldehyde, potassium chloride, ammonium compounds, phosphorus compounds, sulfur, similar plant nutrients and micronutrients, and mixtures and combinations thereof, both synthetic and naturally occurring organic and inorganic materials.

An important function of a broadcast granule formulation includes the release and coverage of the active chemical agent(s) to the surrounding soil after application of the granule. Two mechanisms for releasing active chemical agent(s) contained in or on the granule carrier is: (1) abrasion of the pesticidally active material from the carrier, or alternatively, (2) the granular carrier disintegrates leaving the pesticidally active material in close proximity of the granule origin. In the aforementioned mechanisms, the pesticidally active material is moved away from the granule locus by the dynamic force of water passing the granule locus. A disadvantage to these mechanisms is that the pesticidally active materials that are substantially water-insoluble do not readily associate with the passing water.

A common problem associated with known granules is the inability of the active chemical agent(s) to leave the granule. The inability to leave the carrier is common when the active chemical agent(s) absorbs too deeply into the inert carrier, or the active chemical agent(s) is too tightly adhered to the inert carrier.

Known methods of increasing the coverage of a pesticidally active material to the area surrounding the granule include the use of a dispersable granule that breaks down upon exposure to water to cover a greater surface area, thereby improving distribution of the active chemical agent(s) over a specified area. While these granules improve the area of the active chemical agent coverage, it does not increase the ability of the active chemical agent to migrate further from the outer boundary of the granular carrier. Examples of dry spreadable granules are provided in U.S. Pat. Nos. 6,231,660; 6,375,969; 6,416,775 and 6,613,138.

It would be advantageous to create a granular formulation containing a pesticidally active material that would readily associate with migrating water, thereby increasing the coverage of the pesticidally active material in the soil. The present invention combines the known formulation methods of microemulsions and dry broadcast granules to accomplish this goal.

SUMMARY OF THE INVENTION

The present invention is related to a granular formulation with enhanced biological activity. The granular compositions of the present invention are obtained by coating, absorbing or impregnating a carrier material with a microemulsifiable concentrate formulation containing at least one active chemical agent, wherein the formulation is capable of forming a microemulsion when diluted in water. The granular formulation is a dry composition that may be applied to soil and/or vegetation by spreading or broadcast application. Upon application and subsequent irrigation or rainfall the active chemical agent associates with the water and readily allows the active chemical agent to spread to the surrounding locus. This association allows the active chemical agent to be transported with the passing water, thereby increasing the coverage of the active chemical agent.

DETAILED DESCRIPTION OF THE PREFERRED EMBODIMENTS

The present invention is related a granular formulation with enhanced biological activity. The granular compositions of the present invention are obtained by coating, absorbing or impregnating a carrier material with a microemulsifiable concentrate comprising at least one substantially water-insoluble active chemical agent. The technology further relates to a method for making and using the granular formulation.

In this specification, the term 'active chemical agent' is intended to cover pesticidally active materials as well as materials which are applied to a plant or a locus thereof to achieve a beneficial effect. The agents include, for example, herbicides, bacteriacides, fungicides, insecticides, miticides, acaricides, molluscicides, nematicides, plant growth regulators and insect growth regulators. In the case of plants, the pests will be weeds or other undesirable vegetation in a particular locus. Lower organisms are also included within the scope of the invention, particularly where they are harmful in a particular locus, such as fungi, algae and other micro-organisms. The term pesticidally active materials and pesticides will include substances which control such pests, that is, substances which destroy the pest and/or substances which stop the pest from multiplying or reproducing.

The microemulsifiable concentrate formulations of the present invention which are capable of forming a microemulsion when diluted in water comprise emulsifiers and active chemical agents. The formulations are applied to a granule carrier for use as a dry broadcast granule. As used herein, the term "microemulsifiable concentrate" encompasses concentrates of active chemical agents which, upon dilution in water, form optically transparent formulations having an average emulsion droplet size of between 0.01 and 0.1 micron, even if the emulsion formed upon dilution is not thermodynamically stable. For purposes of this invention, the term "optically transparent" is defined as compositions having no or almost no attenuation of transmitted light, preferably a complete lack of any visible nonuniformity when viewed in mass, in bottles or test tubes, by strong transmitted light. This includes microemulsions that may appear slightly hazy due to the presence of emulsion droplets having an emulsion droplet size at the upper size limits of the described ranges.

The terms "water-insoluble" and "substantially water-insoluble" as used herein mean that for all practical purposes, the solubility of the compound in water is insufficient to make the compound practicably useable in an end-use formulation without some modification either to increase its solubility or dispersability in water.

Substantially water-insoluble active chemical agents, such as pesticides, that are liquid at room temperatures can be dispersed with emulsifiers alone in water without the need for a solvent. In the event that the substantially water-insoluble pesticidally active ingredient is a high viscosity liquid or a solid, solvents may be used to dissolve the substantially water-insoluble pesticidally active ingredient and form a low viscosity liquid. Suitable solvents can be determined by one skilled in the art and include both water-immiscible and water-miscible solvents.

Water-immiscible solvents in which the active chemical agents may be dissolved include aliphatic and aromatic hydrocarbons such as hexane, cyclohexane, benzene, toluene, xylene, mineral oil or kerosene, mixtures or substituted naphthalenes, mixtures of mono- and polyalkylated aromatics commercially available under the registered trademarks SOLVESSO®, ISOPAR®, SHELLSOL®, PETROL SPEZIAL® and AROMATIC®, halogenated hydrocarbons such as methylene chloride, chloroform and o-dichlorobenzene; phthalates, such as dibutyl phthalate or dioctyl phthalate; ethers and esters, such as ethylene glycol monomethyl or monoethyl ether, fatty acid esters; lactones such as butyrolactone; ketones, such as cyclohexanone; higher alcohols such as hexanol and octanol; plant oils such as castor oil, soybean oil, cottonseed oil and possible methyl esters thereof; as well as epoxidised coconut oil or soybean oil. Preferred water-immiscible solvents are aliphatic and aromatic hydrocarbons, petroleum based esters, fatty acid esters (e.g. WITCONOL 2309), dipropyleneglycol monomethylether (e.g. DOWANOL DPM) and castor oil.

Suitable alkyl alkanoate ester solvents include the $C_6$-$C_{13}$ alkyl $C_{1-4}$ alkanoates such as the oxo-hexyl, oxo-heptyl, oxo-octyl, oxo-nonyl, oxo-decyl, oxo-dodecyl and oxo-tridecyl formates, acetates, propanoates, and butanoates; preferably the $C_6$-$C_{13}$ alkyl acetates. These materials are generally commercially available or can be readily made by those of ordinary skill in the art. A number of the foregoing alkyl acetates are commercially available. Particularly advantageous $C_6$-$C_{13}$ alkyl acetates are available from Exxon Mobil Corporation under the general trade designation "EXXATE".

Suitable polyhydric alcohols and polyhydric alcohol condensates include propylene glycol; dipropylene glycol; poly$C_{2-6}$alkylene glycols and derivatives preferably poly-($C_{2-6}$-alkylene) glycol and derivatives such as polypropylene glycol [M.W. 2000-4000], polyoxyethylene polyoxypropylene glycols, polyoxypropylene polyoxyethylene glycols, diethyleneglycol, polyethylene glycol [M.W. 200-4000 amu], methoxy polyethylene glycols 350, 550, 750, 2000, 5000; glycerol; ethoxylated glycerol; propoxylated glycerol; sugar alcohols and their alkoxylated derivatives such as xylitol, mannitol, sorbitol, ethoxylated sorbitol, hydroxypropyl sorbitol; hexylene glycol (2-methyl-2,4-pentanediol); 1,3-butylene glycol; 1,2,6-hexanetriol; ethohexadiol USP (2-ethyl-1,3-hexanediol); $C_{15}$-$C_{18}$vicinal glycol and polyoxypropylene derivatives of trimethylolpropane, short-chain up to 7 carbons, preferably up to 4 carbons aliphatic glycols, and glycerine.

Particularly suitable water-immiscible solvents include methyl esters of fatty acids derived from fats and oils such as methyl oleate, n-octanol, alkyl phosphates such as tri-n-butyl phosphate, propylene carbonate and isoparaffinic solvents.

Water-miscible solvents such as tetrahydrofurfuryl alcohol, gamma-butyrolactone, N-methyl-2-pyrrolidone, tetramethylurea, dimethylsulfoxide, N,N-dimethylacetamide and dimethylformamide may be used as co-solvents with the water-immiscible solvents described above.

The selection of appropriate surfactant(s) for the emulsifier system can be made by one of skill in the art without undue experimentation. Typically, the amount of surfactants needed to form a microemulsion is larger than that for an emulsion. The emulsifier system comprises at least one surfactant capable of forming a microemulsion of the active chemical agents upon dilution in water, for example, at least one non-ionic surfactant such as a condensation product of castor oil and a poly$C_{2-4}$alkylene oxide. Combinations of strongly hydrophobic (HLB>9, preferably >13) non-ionic surfactants and hydrophobic anionic surfactants are also preferred emulsifiers for forming microemulsions.

The term "surfactant" as used in the present specification means a chemical substance that acts as a surface active agent which can provide foaming, wetting, dispersing and emulsifying properties and which is cationic, anionic, nonionic or amphoteric.

As co-surfactants, nonionic surfactants with low HLB or short-chain ($C_4$ to $C_{10}$) alkyl alcohols may be used to lower the HLB of the formulation and to reduce surface tension between water and oil. Solvents, such as fatty acid methyl esters having a carbon chain length of 8 to 12 may provide desired solubility and emulsification characteristics.

Choosing an appropriate surfactant and co-surfactant, if necessary, and the other components of the microemulsifiable concentrate is possible to one of ordinary skill in the art without undue experimentation. A useful guide to preparing microemulsions can be found in U.S. Pat. No. 5,242,907, the contents of which are incorporated herein by reference. The amount of surfactants required to emulsify an oil will depend on the amount of oil in the emulsion, more specifically the interfacial surface area which is proportional to the amount of emulsified oil at a constant particle size.

The emulsifier system can comprise a single surfactant, but in preferred embodiments it is most advantageously a blend of surfactants comprising at least one anionic or cationic surfactant and at least one nonionic surfactant. Preferably, the emulsifier system comprises surfactant(s) in an amount of from about 5% to about 40% by weight of the microemulsifiable concentrate.

Examples of useful surfactants include nonionic surfactants selected from the group consisting of (1) a mono $C_{2-6}$alkyl ether of a poly$C_{2-4}$alkylene oxide block copolymer having at least a first polyalkylene oxide block region and a second polyalkylene oxide block region in which the polyalkylene oxide in said first region is different than the polyalkylene oxide in said second region. Preferably, the $C_{2-6}$alkyl ether portion is a $C_{3-5}$alkyl ether, more preferably a $C_4$alkyl ether, of the alkylene oxide block copolymer. Also preferably, the alkylene oxide block copolymer portion is preferably an ethylene oxide/propylene oxide block copolymer. Preferably the ethylene oxide portion represents from about 10 to about 90 mole % to from about 25 to about 75 mole % of the block copolymer. A particularly preferred material is available under the trade name Ethylan NS-500LQ, available from Akzo Nobel; (2) a condensation product of castor oil and a poly$C_{2-4}$alkylene oxide. Preferably the alkylene oxide portion is ethylene oxide. Preferably the degree of alkoxylation is from about 10 moles to about 100 moles of alkylene oxide per mole of castor oil, more preferably about 20 moles to about 70 moles of alkylene oxide per mole of castor oil. A highly preferred alkoxylated castor oil is available under the trade name Agnique CSO-36, available from Cognis.; (3) a mono- or di-ester of a $C_{12-24}$fatty acid and poly$C_{2-4}$alkylene oxide, where the fatty acid groups may be the same or different. Preferably, the fatty acid groups are the same when two such groups are present. Also preferably, the fatty acid groups are $C_{12-20}$fatty acid groups, more preferably $C_{12-18}$fatty acid groups, most preferably lauroyl, oleic, caprylic or myristoleic. In addition, the poly$C_{2-4}$alkylene oxide portion is preferably polyethoxy and the number of alkylene oxide groups in the poly$C_{2-4}$alkylene oxide portion is preferably from about 2 to about 40 repeating units. Highly preferred materials of this type include Kessco PEG 400DL (Stepan) and Emerest 2620 (Cognis).

In a particular embodiment, the formulation of the present invention comprises, as a non-ionic surfactant, a copolymer of propylene oxide (PO) and ethylene oxide (EO) and/or an ethoxylated tristyrene phenol. A suitable copolymer of PO and EO is alpha-butyl-omega-hydroxypoly(oxypropylene) block polymer with poly(oxyethylene) and has a molecular weight of 2400 to 3500. Commercially available examples of this copolymer are Toximul®, Witconol® and Atlas®. In a particular embodiment of the present invention, the copolymer is present in the microemulsifiable concentrate at between about 0.5 and about 10 weight % and preferably at about 1 to 5 weight %. A suitable ethoxylated tristyrene phenol is alpha-[2,4,6-tris[1-(phenyl)ethyl]phenyl]-omega-hydroxy poly(oxyethylene). Suitably, the poly(oxyethylene) content averages from about 4 to about 150 moles. A commercially available example of this surfactant is Soprophor BSU®. In a particular embodiment, this surfactant is present in the concentrate at between about 1 and about 15 weight % and preferably from 6 to 10 weight %.

Suitable anionic surfactants include a poly(oxy-1,2-ethanediyl)-alpha-$C_{10-15}$alkyl-omega-hydroxy phosphate or sulphate and/or a $C_{10-13}$alkylbenzenesulfonic acid. Preferably, the a poly(oxy-1,2-ethanediyl)-alpha-$C_{10-15}$alkyl-omega-hydroxy phosphate or sulphate is a poly(oxy-1,2-ethanediyl)-alpha-tridecyl-omega-hydroxy phosphate or sulphate. Also, the (oxy-1,2-ethanediyl) portion of the compound is present in about 3 to about 9, preferably about 6, repeating units per molecule. A suitable compound for the poly(oxy-1,2-ethanediyl)-alpha-$C_{10-15}$alkyl-omega-hydroxy phosphate is available as Stepfac 8181 (Stepan). A suitable compound for the $C_{10-13}$alkylbenzenesulfonic acid is Biosoft S-100 (Stepan). Additional suitable anionic surfactants include the phosphate and sulphate derivatives of ethoxylated alkyl phenols such as -[EO]$_{2-20}$— di and tristyrylphenols, nonylphenols, dinonylphenol and octylphenols.

Where salts of the phosphate or sulphate group are desirable, the salt may be a salt with any base so long as the base is not incompatible with any of the other ingredients including the active chemical agent(s). Particularly suitable are the phosphate salts of alkali metals, alkaline earth metals, ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine.

In another embodiment, the anionic surfactant is a styrylphenol polyethoxyester phosphate. A suitable anionic surfactant is alpha-[2,4,6-tris[1-(phenyl)ethyl]phenyl]-omega-hydroxy poly(oxyethylene) ester phosphate. In particular, this compound is present as a mixture of the monohydrogen and dihydrogen phosphate esters and the corresponding ammonium, calcium, magnesium, potassium, sodium and zinc salts. Suitably, the poly(oxyethylene) content averages from about 4 to about 150 moles. A commercially available example of this surfactant is Soprophor 3D33®. In a particular embodiment, this surfactant is present at between about 5 and about 10 weight %.

Cationic surfactants suitable for use in the present invention include polyC$_{2-4}$alkoxylated C$_{14-20}$fatty amines, preferably the polyC$_{2-4}$alkoxylated C$_{12-18}$fatty amines, most preferably a polyC$_{2-4}$alkoxylated tallow amine. The polyC$_{2-4}$alkoxylated portion of this component is preferably present in either 2-8 (more preferably 2-5) repeating units per molecule or the polyC$_{2-4}$alkoxylated portion of this component is preferably present in about 14 to about 18 (more preferably about 16) repeating units per molecule or more preferably is -[EO]$_{2-20}$—; and mixtures thereof. Particularly useful amine compounds include the Toximuls such as TA-2, -3, -4, -5, -6, -7, -7, -8, -9, -10, -11, -12, -13, -14, -15, -16, -17, -18, -19 and -20 (Stepan); and mixtures thereof. Additional suitable cationic surfactants include the fatty acid alkanol amides such as, for example, the Witcamides (Witco).

Preferred water-insoluble active chemical agents include those pesticides that are substantially water-insoluble active chemical agent, sometimes referred to herein for brevity as a "water-insoluble" active ingredient even if it has measurable solubility in water. This active ingredient preferably has a solubility in deionized water at 20° C. not greater than about 5000 mg/l. Especially preferred water-insoluble active ingredients useful in the present invention have a solubility in deionized water at 20° C. not greater than about 2000 mg/l.

Pesticides and pesticidally active materials include, without being limited to, herbicides, fungicides, insecticides, miticides, acaricides, molluscicides, nematicides, bacteriacides, plant growth regulators and insect growth regulators. Suitable substantially water-insoluble active ingredients suitable for use in the present invention include, but are not limited to the pesticides set forth herein as well as mixtures thereof. The common name used to designate the individual compounds may be found in various sources including The Pesticide Manual, 12th edition, 2000, British Crop Protection Council.

Fungicides useful in the present invention include azoxystrobin, bitertanol, chlorothalonil, cyproconazole, cyprodinil, difenoconazole, fenpiclonil, fenpropidin, fenpropimorph, fludioxonil, furalaxyl, mefenoxam (r-metalaxyl), metalaxyl, myclobutanil, oxadixil, penconazole, propiconazole, pyrifenox, pyroquilon, thiabendazole, thiophanate-methyl, triadimefon, triadimenol and trifloxystrobin;

Insecticides useful in the present invention include abamectin, bifenthrin, bromopropylate, carbaryl, chlorpyrifos, clothianidin, gamma-cyhalothrin, lambda-cyhalothrin, cypermethrin, beta-cypermethrin, cyromazine, difenthiuron, emamectin benzoate, fenoxycarb, tau-fluvalinate, furathiocarb, imidacloprid, lufenuron, methidathion, organophosphorus compounds, permethrin, profenofos, pymetrozine, tefluthrin, thiacloprid and thiamethoxam;

Herbicides useful in the present invention include acetochlor, ametryne, butafenacil, chlortoluron, clodinafop, dimethachlor, dimethenamid, dimethenamid-P, fenclorim, fluazifop-butyl, fluazifop-p-butyl, flumeturon, flumetsulam, mesotrione, metolachlor, S-metolachlor, norflurazon, pretilachlor, prodiamine, prometryne and pyridate;

Growth regulators such as cimectacarb, flumetralin, paclobutrazol and trinexapac-ethyl;

Safeners such as fluxofenime, benoxacor, cloquintocet mexyl, dichlormid, flurazole; and Plant activators such as acibenzolar-s-methyl.

Granular materials suitable for use in preparing granular formulations of the present invention include those described in U.S. Pat. Nos. 4,015,973; 4,954,134; 5,019,564; 5,078,779; 5,207,389; 5,228,895; 5,242,690; 5,739,081; 6,180,565; 6,231,660; 6,375,969; 6,416,775; 6,579,831; 6,613,138, and U.S. Patent Application Publication No. 2005/0113257, the contents of which are incorporated herein by reference.

Granular formulations offer significant advantages in packaging, ease of handling and safety, relative to liquid formulations. While not being limited to any particular sizes, the granules of the present invention typically have an average particle size in the range of about 0.1 to about 10 mm, preferably between about 0.25 to about 5 mm, and more preferably between about 0.5 to about 3 mm, although sizes outside of this range can be used.

The granules can be in virtually any desired shape, for example, spheres, cylinders, ellipses, rods, cones, discs, needles and irregular shapes. Ideally, the granules are approximately spherical and have a smooth surface, which lends to desired flow characteristics of the granules in bulk form.

Small granules, for example, granules about 0.1 to about 3 mm in diameter, preferably of uniform size, tend to be free flowing and low dusting. Although granular compositions can have high bulk densities, for example, greater than 60 pounds per cubic foot, it is sometimes advantageous to use smaller granules with a lower bulk density to efficiently transport and distribute the required amount of pesticidally active material without excessive amounts of inert carrier.

Preferably the granules retain their physical integrity during handling and spreading, and, in the case of dispersible granules, typically disintegrate when irrigation water is applied or rainfall hits the particle. Upon wetting, these granules may disintegrate (bloom) to cover the soil surface. This bloom can cover an area many times the original area covered by the granule.

The microemulsifiable concentrates may be applied to the granules such that the active chemical agents can be loaded in an amount up to about 30 weight percent of the granules. The active chemical agents can be homogeneously distributed throughout the granule, spray impregnated into, or coated onto the granules.

In addition to the components of the microemulsifiable concentrate, generally, the granules can include fillers (also referred to as a carrier), surface active agents (which term can include dispersants and wetting agents) and auxiliary agents such as binders, stabilizers and buffering agents. The filler can be inert, or can serve a biological function, such as acting as a fertilizer. The filler, as well as the other components, preferably should not degrade the pesticidally active material during the granule preparation or on long term storage or use in the field. Those of skill in the art can readily select appropriate granule components to satisfy these criteria.

Typically, the filler particles are finely divided filler particles, and can include inert mineral fillers. The particle size of the filler will depend upon the ultimate use of the granule.

The absorbency of the granules is believed to result in part from inclusions of voids between the finely divided particles. Accordingly, the degree of packing will influence the degree of absorbency of the granules. The absorbency can also be varied by choosing different fillers that affect the packing. The degree of absorbency can be fine tuned further by using a mixture of different fillers. For example, heat processed expanded perlite fillers tend to lead to highly absorbent granules while mica or talc fillers lead to less absorbent granules. The degree of absorbency of a granule can thus be varied by varying the ratio of heat processed perlite to mica.

The fillers can be inert compounds that, upon application, break down over time, but provide no other properties, or they can themselves provide a useful function beyond merely breaking down over time to release the pesticidally active material.

In one aspect, the fillers are water-insoluble. The finely divided filler itself can be absorbent, as in the case of diatomaceous earth, attapulgite or zeolites, but this is not essential as it is the overall absorbency of the granule rather that of the individual particles that is important to the working of the invention. However, the overall absorbency of granules usually increases when absorbent particles are used.

Inert fillers or carriers include mineral components such as dolomite and limestone, light weight additives such as expanded silica, fly ash, hydrated lime, wheat flour, wood flour, ground wheat straw, cellulose and soy flour. Mineral earths and clays such as bentonite, kaolin, attapulgite, diatomaceous earth, zeolites, calcium carbonate, talc, muscovite mica and manufactured materials such as precipitated silicas and silicates, fused sodium potassium, aluminum silicate (heat processed perlite) or organic materials such as coals, lignites and plastics can also be used. Preferred materials include heat processed perlite, talc and muscovite mica, and combinations of such materials. The generally plate-like particle shape of these materials enables them to separate from each other more readily when granules (manufactured by extrusion, pan granulating or other means) are dispersed in water. Additional fillers include finely milled wood particle board, which includes approximately about 10 wt % of a urea-formaldehyde resin, and wheat straw flour resulting from finely milled wheat straw particle board, which includes a diphenylmethane diisocyanate resin. In both cases, the additional resin can assist in producing a granular substrate that does not degrade during handling but breaks down upon exposure to water. Other inert compounds meeting the bulk density and sizing specifications can also be used.

In one aspect of the invention, the filler functions as a fertilizer. Fertilizers typically provide at least one of the plant nutrients nitrogen, phosphate or potassium. Representative carriers that function as fertilizer components include urea, sulfur-coated urea, isobutylidene diurea, ammonium nitrate, ammonium sulfate, ammonium phosphate, triple super phosphate, phosphoric acid, potassium sulfate, potassium nitrate, potassium metaphosphate, potassium chloride, dipotassium carbonate, potassium oxide and a combination of these. Soil nutrients include calcium, magnesium, sulfur, iron, manganese, copper, zinc; oxides thereof, salts thereof and combinations thereof. Amendment materials include natural organic products such as humic acid, blood meal, bone meal, seed meal, feather meal and soy meal; meat meal; animal waste from various animal sources; activated sludge, hydrolyzed animal hair; fish byproducts; chitin; composts; and combinations thereof.

A binder may be used to agglomerate the components of the granules. When present, the binder can be typically used in amounts up to about 20 percent by weight (dry basis) of the granular composition, more typically between about 2 to about 20 percent by weight. The binder binds the ingredients into a granular substrate which resists attrition and will not rapidly degrade, and therefore substantially maintains particle size during handling. Examples of suitable binders include brewers condensed solubles, lignosulfonate, sodium carbonate lignin, cane molasses, beet syrup, beet molasses, desugared beet molasses, whey, starch, soy solubles with cane molasses or the like, hydrolyzed collagen, amino acid solutions, cellulose derivatives, or cellulose based polymer binders. Other water soluble binders having equivalent properties to, for example, brewer's condensed solubles, can also be used.

The binder can be added to the composition as a solution. The solution is typically provided as a water-based slurry having about 40 to about 50 percent solids by weight and weighing about 10 pounds per gallon. The binder can also be added and mixed with the other dry ingredients, subsequently mixing in an amount of water.

Additional auxiliary agents such as surfactants, dispersants, disintegrating agents, wetting agents and the like, can be added where desired to modify the properties of the granules.

UK Patent 1,304,54 describes four basic methods for preparing granular formulations. The four methods are extrusion; applying a surface coating onto a granule; absorbing an active substance into a granule; and applying a binder and active material to a suitable powder and forming granules from the powder mix.

The granules can be prepared via an extrusion process, for example, by extruding a premix of the microemulsifiable concentrate and other ingredients under relatively high pressure, (typically in excess of 100 psi), and cutting the resulting extrudate into short lengths. The resulting granules can then be dried.

In this process, the individual components can be combined in any sequence and blended in a suitable blender and granulated using known methods and equipment for making granules. For example, the finely divided filler and dispersant can be blended together with water being added before, during or after the blending of the dry ingredients. Alternatively, the dispersant can be dissolved first in the water used for blending. The microemulsifiable concentrate comprising the active chemical agent(s) can be combined with the other components used to form the granules prior to extrusion. After the granules are formed, they are then dried to remove the excess moisture. Granules that are prepared in the absence of the active chemical agent by an extrusion process can subsequently be sprayed with the microemulsifiable concentrate comprising the active chemical agent(s) to adhere the agent(s) to the granules. The sprayed granules are then dried, for example in a fluid-bed dryer, to the desired moisture content.

Granules can also be prepared by coating a core granule with an absorbent coating of filler particles. A microemulsifiable concentrate comprising the chemically active materials can then be loaded onto the surface layer of the granules. The amount of water used can vary depending on the desired absorptive capacity of the inert granules, which can be controlled by varying the ratio of the fillers. Granulating conditions can also have an influence on the amount of water required. Typically the amount of water can range from about 5 kg to about 150 kg per 100 kg dry mix (fillers and dispersant) and more typically is about 20 to about 70 kg water/100 kg dry mix.

UK Patent 1,304,543 discloses a process in which absorbent granules are prepared, and solutions of active substances, or liquid substances, are absorbed into the granules. These compositions have granules which are calcined zeolites of several hundred microns in diameter.

Pre-formed granules can be stored, and then used to take up a predetermined amount of the pesticidally active material at an appropriate time and place. The microemulsifiable concentrates of the present invention can be sprayed onto the granules, for example, in a manner to distribute the substance over the surface of the absorbent granules as quickly as possible. The spray can be introduced through air atomizing nozzles to ensure even spread of the liquid active substance the granules. Flat spray jets will in some cases be appropriate. The amount of pesticidally active material that is absorbed onto the granule will vary dependent upon the desired end use as well as the granules ability to absorb the formulations.

When loading the preformed granules with the active chemical agents, a uniform loading per granule can be achieved. Equilibration between unevenly loaded granules is believed to take place but this can take substantial periods of time. Where the absorbency of the granule is to be substantially fully saturated then the liquid can simply be poured onto the granules and granules agitated until they become fully saturated.

Preferably, the granules are partially saturated. For example, when the loading capacity is about 40 percent, it is preferred to only load to about 32 percent, i.e. about 80 percent of its capacity. It is preferable to load the granules to about 60 to about 90 percent and more preferably about 70 to about 85 percent of their capacity. That said, since the pesticidally active materials are effective at relatively low concentrations, and the fertilizers are applied at relatively high concentrations, the weight ratio of pesticidally active materials to the rest of the granule components is often relatively low.

Many dry bulk granular fertilizers, and other inert granules, can be impregnated or coated with the microemulsifiable concentrates of the present invention. When applying the microemulsifiable concentrates of the present invention to dry bulk granular fertilizers, one should follow all directions for use and precautions on the respective product labels, regarding target crops, rates per acre, soil texture, application methods (including timing of application) and rotational crops, to ensure that the granules are compatible with the anticipated use of the compositions.

The granule formulations can be prepared, for example, using any closed drum, belt, ribbon, or other commonly used dry bulk fertilizer blender. Nozzles used to spray microemulsifiable concentrates onto the granules are ideally placed in an appropriate position, and aimed appropriately, to provide uniform spray coverage. Care should be taken to aim the spray directly onto the granules, and to avoid spraying the walls of the blender.

Those skilled in the art can readily determine how much chemically active ingredient to add to the granules. For example, one can simply consider the application rate of the granules in their intended use (for example, as a fertilizer), and the application rate of the chemically active ingredient, and determine an appropriate ratio by which to add such materials to the granules.

The granules can also be prepared by forming a wettable powder by blending the ingredients, optionally including the microemulsifiable concentrate, and milling them to provide the desired particle size, then subsequently forming the powder into granules by a range of techniques including agglomeration, spray drying, or other means such as pan granulation.

The granules may be prepared by mixing and pelletizing the individual components, and the mixing can be done at relatively low shear forces to avoid degrading the individual components. The pelletizing can be accomplished using conventional pelletizing equipment, such as pelletizing pans and drum granulators. The resulting granules, in pellet form, are then generally dried to remove excess moisture. Granules that are prepared in the absence of the active chemical agent by an extrusion process can subsequently be sprayed with microemulsifiable concentrates comprising the active chemical agent(s) to adhere the agent(s) to the granules.

The granules can be dried using any suitable means (e.g. on trays) that does not result in attrition or damage. They can be dried under elevated temperature and/or under vacuum. Band or static bed dryers can be used, although fluid bed dryers and rotary drum dryers can be preferred because of their relative efficiency.

The resulting granules can then be screened, if desired, to remove oversized and undersized granular substrates. The improperly sized material can be recycled to the mixing stage or milled to the appropriate size and re-screened. Optionally, the finished product can be sprayed with a light weight mineral oil to prevent dusting of the product in bulk form.

The sizing and bulk density finished product specifications will impact how the granules can be applied. The granule size can be determined, for example, by the size guide number/uniformity index system used in the fertilizer industry. The size guide number describes the relative particle size and is obtained by multiplying the average particle size, in millimeters, by 100. The uniformity index is a comparison of large particles to small particles. The index is expressed as a whole number between 1 and 100 with higher numbers indicating better uniformity and tighter size range. Additionally, the sizing can be determined in accordance with ASTM E 728-91 Volume 11.04 wherein the sizing is preferably 20% or more passing through a 14 mesh screen and retained on a 40 mesh screen.

The manufactured granular substrate ideally is strong enough that the particle does not degrade during normal conveying and handling operations. The degradation of granular substrates would result in an increase in fine material which in turn would increase the bulk density. Additionally, dust or powder material absorbs more chemical agent and therefore would result in the improper distribution of the active chemical agent upon application.

Preferably, the granular substrate will not degrade until subjected to water. Degradation also should be minimized when subjected to high humidity.

The granules can be applied with a dry spreader, such as a rotary or drop spreader, to a target area. The active chemical agents can then associate with water, whether user-applied or natural, such as rain or dew, and readily spread to the surrounding locus.

The present invention will be better understood with reference to the following non-limiting examples.

Liquid, microemulsifiable concentrate formulations 1 and 2 were prepared by combining the solvents in a mixer and starting the mixer. The surfactants were warmed in order to reduce their viscosity and added to the mixer. Molten lambda-cyhalothrin technical was then added and the composition was mixed until homogeneous. The carrier granules used were uniform, round granules composed mainly of wood dust and dolomitic limestone with an average diameter of 1.5 mm. The granules were charged to a Munsen type mixer. While mixing, the liquid microemulsifiable concentrations were sprayed onto the granules.

| Microemulsifiable concentrate 1 (MEC 1) | | |
| --- | --- | --- |
| Ingredient | Function | Wt. % |
| Methyl oleate | Solvent | 43.2 |
| Tetrohydrofurfuryl alcohol | Co-solvent | 43.1 |
| Butyl ether derivative of EO/PO block copolymer (Toximul ® 8320 available from Stepan) | Non-ionic surfactant | 10.0 |
| Tristyrylphenol ethoxylate phosphate ester (Soprophor ® 3D33 available from Rhodia) | Anionic surfactant | 2.0 |
| Lamba cyhalothrin technical (93.1%) | Active ingredient | 1.6 |

| Microemulsifiable concentrate 2 (MEC 2) | | |
|---|---|---|
| Ingredient | Function | Wt. % |
| Propylene carbonate | Solvent | 69.1 |
| Tetrohydrofurfuryl alcohol | Solvent | 17.3 |
| Butyl ether derivative of EO/PO block copolymer (Toximul ® 8320 available from Stepan) | Non-ionic surfactant | 10.0 |
| Tristyrylphenol ethoxylate phosphate ester (Soprophor ® 3D33 available from Rhodia) | Anionic surfactant | 2.0 |
| Lamba cyhalothrin technical (93.1%) | Active ingredient | 1.6 |

A granular material comprising lamba-cyhalothrin, outside of the scope of the present invention and described below as Comparative Granule 1, was prepared as described above, with the exception that the composition contained no surfactants.

| Comparative Granule 1 (Comp 1) | | |
|---|---|---|
| Ingredient | Function | Wt. % |
| Methyl oleate | Solvent | 49.2 |
| Tetrohydrofurfuryl alcohol | Co-solvent | 49.2 |
| Lamba cyhalothrin technical (93.1%) | Active ingredient | 1.6 |

The above formulations were applied onto carrier granules which were uniform, round granules composed mainly of wood dust and dolomitic limestone with an average diameter of 1.5 mm. The formulations were applied targeting a granule containing 0.045 wt % lambda-cyhalothrin.

A known amount of treated carrier was added to a 100 mL cylinder and approximately 75 mL of water was added on top of the carrier and allowed to sit for 20 seconds with no agitation. The supernatant was removed with a long plastic pipette and filtered through a 0.2 micron filter to remove any suspended particles. The filtered supernatant was assayed for lambda-cyhalothrin. The lambda-cyhalothrin extraction results set forth in Table 1 represent the concentration of lambda-cyhalothrin found in the supernatant in micrograms per milliliter.

TABLE 1

| Concentration of lambda-cyhalothrin in water (µg/mL) | | |
|---|---|---|
| MEC 1 | MEC 2 | COMP 1 |
| 2 | 7 | 0.2 |

As can be seen from the data in Table 1, the granular formulations of the present invention release the lambda-cyhalothrin much more readily than a similar formulation that does not contain an emulsifier system. This enables the active ingredient to more readily associate with migrating water, thereby increasing the coverage of the pesticidally active material in the target area.

The following procedures were used to prepare active ingredient treated granules and to measure the release of active ingredient into water migrating through the granules.

Spray solutions were prepared as follows: Soprophor® BSU—tristyrylphenol ethoxylate with approximately 16 moles ethoxylation available from Rhodia, Soprophor® 3D33 and Toximul® 8320 were heated in an oven at 50° C. overnight to melt and fluidize the surfactants and inverted several times to mix before use. The same was done for the Lambda cyhalothrin and Propiconazole technicals but at 75° C. The solvents, THFA and/or propylene carbonate, were added to a clean stainless beaker. While stirring with a magnetic stirrer, all remaining ingredients were added. The solutions were allowed to mix until all ingredients were fully dissolved.

Granules were prepared as follows: 200 grams of 8/16 sized Agsorb LVM granules were placed in a baffled tumbler. The tumbler was started and the spray solutions were applied using a conventional trigger sprayer to the curtain of falling granules. The amount of liquid applied was determined gravimetrically by weighing the spray bottle after each spray until the desired amount of product was applied. After application, the granules were allowed to tumble for approximately 15 minutes. A new spray bottle was used for each solution to prevent contamination from previous solutions.

A 24 cm Whatman paper filter (#5) was folded into a cone and placed in a clean plastic funnel that was large enough to accommodate the filter. The filter was pre-wetted with 3 mL of tap water to adhere the filter to the funnel as is common practice. 75 grams of granules were added to the filter. 110 mL of tap water was poured on top of the granules. A small glass jar was placed under the funnel to catch the passing water. Once 25 mL had passed through, the jar was removed and capped. The amount of active ingredient in the water phase was measured via analytical methods. For the sample prepared with lambda cyhalothrin formulations, the tap water was acidified with 0.1% acetic acid to prevent hydrolysis of the lambda cyhalothrin while awaiting chemical analysis. This water was used for both lambda cyhalothrin formulated granules for consistency. Details regarding the spray solutions, treated granules and analytical results showing the active ingredient content in the aqueous phase are set forth below.

Formulations Used to Study Enhanced Release of Active Ingredient from Granules

| Spray solutions | | | | | | |
|---|---|---|---|---|---|---|
| Ingredient | A wt % | B* wt % | C wt % | D* wt % | E wt % | F* wt % |
| THFA | 17.3 | 17.3 | 17.3 | 17.3 | | |
| Propylene carbonate | 69.0 | 81.0 | 69.1 | 81.1 | 73.5 | 93.5 |
| Toximul 8320 | 10.0 | | 10.0 | | | |
| Soprophor 3D33 | 2.0 | | 2.0 | | 10.0 | |
| Soprophor BSU | | | | | 10.0 | |
| Lambda cyhalothrin (88%) | 1.7 | 1.7 | | | | |
| Propiconazole (95%) | | | 1.6 | 1.6 | | |
| Azoxystrobin (97.8%) | | | | | 6.5 | 6.5 |
| total | 100.0 | 100.0 | 100.0 | 100.0 | 100.0 | 100.0 |

| Treated granules | | | | | | |
|---|---|---|---|---|---|---|
| Ingredient | A wt % | B* wt % | C wt % | D* wt % | E wt % | F* wt % |
| Agsorb granules | 93.0 | 93.0 | 93.0 | 93.0 | 90.9 | 90.9 |
| solution A | 7.0 | | | | | |
| Solution B | | 7.0 | | | | |
| Solution C | | | 7.0 | | | |
| Solution D | | | | 7.0 | | |
| Solution E | | | | | 9.1 | |
| Solution F | | | | | | 9.1 |
| total | 100.0 | 100.0 | 100.0 | 100.0 | 100.0 | 100.0 |

*Comparative Examples: Compositions outside of the scope of the present invention Analytical Results of Active Ingredient Content (µg a.i./mL) in the Water Phase

| Formulation | µg a.i./mL | |
| --- | --- | --- |
| A | 10 | |
| B* | <1 | (too low to determine precisely) |
| C | 9.7 | |
| D* | 1.2 | |
| E | 18.3 | |
| F* | 5.3 | |

As can be seen from the above data, the granular formulations of the present invention release the active ingredients much more readily than a similar formulation that does not contain an emulsifier system. This enables the active ingredient to more readily associate with migrating water, thereby increasing the coverage of the pesticidally active material in the target area.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

I claim:

1. A dry spreadable or broadcast granule comprising:

i) a solid carrier;

ii) at least one substantially water-insoluble active chemical agent; and iii) an emulsifier system capable of forming a microemulsion of the at least one substantially water-insoluble active chemical agent (ii) upon dilution in water.

2. The granule of claim 1 wherein the substantially water-insoluble active chemical agent comprises at least one pesticide.

3. The granule of claim 2 wherein the substantially water-insoluble active chemical agent comprises at least one pesticide selected from the group consisting of herbicides, fungicides, insecticides, miticides, acaricides, molluscicides, nematicides, bacteriacides, plant growth regulators and insect growth regulators.

4. The granule of claim 1 wherein the active chemical agent has a water solubility in deionized water at 20° C. of not greater than 5000 mg/l.

5. The granule of claim 1 wherein the emulsifier system comprises at least one non-ionic surfactant.

6. The granule of claim 5 wherein the emulsifier system comprises a condensation product of castor oil and a poly $C_{2-4}$alkylene oxide.

7. The granule of claim 1 wherein the emulsifier system comprises at least one non-ionic surfactant having an HLB>9 and at least one hydrophobic anionic surfactant.

8. The granule of claim 1 wherein the solid carrier is an inert material.

9. The granule of claim 6 where the solid carrier is a dispersible granule.

10. The granule of claim 1 wherein the solid carrier is a fertilizer material.

11. A method of making dry spreadable or broadcast granules containing at least one active chemical agent, said method comprising applying to or incorporating into a solid carrier i) at least one substantially water-insoluble active chemical agent; and ii) an emulsifier system capable of forming a microemulsion of the at least one substantially water-insoluble active chemical agent upon dilution in water.

12. The method of claim 11 wherein the substantially water-insoluble active chemical agent comprises at least one pesticide.

13. The method of claim 12 wherein the substantially water-insoluble active chemical agent comprises at least one pesticide selected from the group consisting of herbicides, fungicides, insecticides, miticides, acaricides, molluscicides, nematicides, bacteriacides, plant growth regulators and insect growth regulators.

14. The method of claim 11 wherein the active chemical agent has a water solubility in deionized water at 20° C. of not greater than 5000 mg/l.

15. The method of claim 11 wherein the emulsifier system comprises at least one non-ionic surfactant.

16. The method of claim 15 wherein the emulsifier system comprises a condensation product of castor oil and a poly $C_{2-4}$alkylene oxide.

17. The method of claim 11 wherein the emulsifier system comprises at least one non-ionic surfactant having an HLB>9 and at least one hydrophobic anionic surfactant.

18. The method of claim 11 wherein the solid carrier is an inert material.

19. The method of claim 18 where the solid carrier is a dispersible granule.

20. The method of claim 11 wherein the solid carrier is a fertilizer material.

21. The method of making dry spreadable or broadcast granules according to claim 11, said method comprising:

i) preparing at least one microemulsifiable concentrate comprising at least one substantially water-insoluble active chemical agent and an emulsifier system; and ii) applying the microemulsifiable concentrate to or incorporating the microemulsifiable concentrate into a solid carrier.

22. A method of delivering an active chemical agent to a site to be treated, said method comprising i) applying upon the site a dry spreadable or broadcast granular composition comprising a) a carrier;

b) at least one substantially water-insoluble active chemical agent; and c) an emulsifier system capable of forming a microemulsion of the substantially water-insoluble active chemical agent (b) upon dilution in water; and ii) allowing said dry granular composition to be contacted with water.

23. The method of claim 22 wherein the substantially water-insoluble active chemical agent comprises at least one pesticide.

24. The method of claim 22 wherein the substantially water-insoluble active chemical agent comprises at least one pesticide selected from the group consisting of herbicides, fungicides, insecticides, miticides, acaricides, molluscicides, nematicides, bacteriacides, plant growth regulators and insect growth regulators.

25. The method of claim 22 wherein the active chemical agent has a water solubility in deionized water at 20° C. of not greater than 5000 mg/l.

26. The method of claim 22 wherein the emulsifier system comprises at least one non-ionic surfactant.

27. The granule of claim 26 wherein the emulsifier system comprises a condensation product of castor oil and a poly $C_{2-4}$alkylene oxide.

28. The method of claim 22 wherein the emulsifier system comprises at least one non-ionic surfactant having an HLB>9 and at least one hydrophobic anionic surfactant.

29. The method of claim 22 wherein the solid carrier is an inert material.

30. The method of claim 29 where the solid carrier is a dispersible granule.

31. The method of claim 22 wherein the solid carrier is a fertilizer material.

* * * * *